(12) United States Patent
Song et al.

(10) Patent No.: US 12,372,716 B1
(45) Date of Patent: Jul. 29, 2025

(54) INTEGRATED OPTICAL WAVEGUIDE DEVICE, ENDOSCOPIC PROBE, AND ALL-OPTICAL PHOTOACOUSTIC ENDOSCOPY (PAE) SENSING SYSTEM

(71) Applicant: ZHEJIANG LAB, Hangzhou (CN)

(72) Inventors: Qianqian Song, Hangzhou (CN); Yong Yang, Hangzhou (CN)

(73) Assignee: ZHEJIANG LAB, Hangzhou (CN)

( * ) Notice: Subject to any disclaimer, the term of this patent is extended or adjusted under 35 U.S.C. 154(b) by 0 days.

(21) Appl. No.: 18/988,971

(22) Filed: Dec. 20, 2024

(30) Foreign Application Priority Data

Aug. 28, 2024 (CN) .......................... 202411191179.3

(51) Int. Cl.
*G02B 6/12* (2006.01)
*A61B 5/00* (2006.01)
(Continued)

(52) U.S. Cl.
CPC .............. *G02B 6/12* (2013.01); *A61B 5/0095* (2013.01); *G01H 9/004* (2013.01); *G01N 21/1702* (2013.01); *G02B 2006/12138* (2013.01)

(58) Field of Classification Search
CPC .................. G02B 6/12; G02B 6/12004; G02B 2006/12138; A61B 5/0095; G01H 9/00;
(Continued)

(56) References Cited

U.S. PATENT DOCUMENTS

| 11,378,552 B2 * | 7/2022 | Singh .................... A61B 8/4483 |
| 2002/0122651 A1 * | 9/2002 | Roberts .................. G02B 6/105 385/11 |

(Continued)

FOREIGN PATENT DOCUMENTS

CN 114159022 A 3/2022

OTHER PUBLICATIONS

W. Bogaerts et al. Compact wavelength-selective functions in silicon-on-insulator photonic wires. IEEE Journal of Selected Topics in Quantum Electronics, 12:6:1394-1401, Nov./Dec. 2006 (https://doi.org/10.1109/JSTQE.2006.884088) (Year: 2006).*

(Continued)

*Primary Examiner* — Michael Stahl
(74) *Attorney, Agent, or Firm* — Bayramoglu Law Offices LLC (57) ABSTRACT

An integrated optical waveguide device, an endoscopic probe, and an all-optical photoacoustic endoscopy (PAE) sensing system are provided. The integrated optical waveguide device features a core layer that sequentially includes a splitter, a first wavelength transmission region, and a sensing reflection region, all connected along the light transmission direction. The splitter is configured to separate light of different wavelengths. The first wavelength transmission region is configured to transmit pulsed light, while the sensing reflection region is configured to realize transmission, reflection or resonance of a light signal at a preset wavelength. By monitoring changes in the resonant or reflective wavelength, environmental parameter changes can be monitored. In the endoscopic probe, the integrated optical waveguide device enables signal and function separation, the sensed light signal and the pulsed light signal share the same double-clad fiber, which make the probe more compact and enhances its sensitivity.

12 Claims, 3 Drawing Sheets

(51) Int. Cl.
*G01H 9/00* (2006.01)
*G01N 21/17* (2006.01)

(58) Field of Classification Search
CPC . G01H 9/004; G01N 21/1702; G01N 29/2418
See application file for complete search history.

(56) References Cited

U.S. PATENT DOCUMENTS

| | | | |
|---|---|---|---|
| 2020/0319019 A1* | 10/2020 | Westerveld | G01H 9/004 |
| 2021/0055473 A1 | 2/2021 | Shnaiderman et al. | |
| 2022/0397388 A1* | 12/2022 | Zhang | G01B 11/161 |
| 2023/0003939 A1* | 1/2023 | Bogaerts | G02B 6/4215 |
| 2023/0055692 A1* | 2/2023 | Van Der Heiden | G01D 5/35335 |
| 2023/0059011 A1 | 2/2023 | Harmsma et al. | |

OTHER PUBLICATIONS

Sun Mingli, et al., New Light in Microscopic Exploration: Portable Photoacoustic Microscopy (Invited), Laser & Optoelectronics Progress, 2024, pp. 1-16, vol. 61, No. 6.

\* cited by examiner

INTEGRATED OPTICAL WAVEGUIDE DEVICE, ENDOSCOPIC PROBE, AND ALL-OPTICAL PHOTOACOUSTIC ENDOSCOPY (PAE) SENSING SYSTEM

CROSS REFERENCE TO THE RELATED APPLICATIONS

This application is based upon and claims priority to Chinese patent application No. 202411191179.3, filed on Aug. 28, 2024, the entire contents of which are incorporated herein by reference.

TECHNICAL FIELD

The present disclosure relates to the field of photoacoustic endoscopy (PAE) imaging, and more specifically, to an integrated optical waveguide device, an endoscopic probe, and an all-optical PAE sensing system.

BACKGROUND

Early diagnosis and early treatment in initial occurrence of major diseases are considered effective ways to improve the curative probability, lighten the economic burden on patients, and alleviate pain. With development of optical imaging, photoacoustic imaging (PAI) is a non-destructive, non-invasive, and high-sensitive novel medical imaging technique. As an important technique in the PAI, photoacoustic detection is realized with an ultrasonic transducer. In interior cavities, a complex application environment where PAE formed by combining PAI with fiber-optic endoscopy imposes increasingly high requirements on miniaturization of the piezoelectric transducer, and also promotes the development of the piezoelectric transducer. The sensitivity of the piezoelectric transducer is directly proportional to a square of the device size, while the limit of detection (LOD) of the piezoelectric transducer is inversely proportional to the device size. The piezoelectric transducer has a relatively high LOD, which causes image noises. In addition, the piezoelectric transducer is required to further miniaturize due to its opacity when designing the PAE, but it would limit the sensitivity and the detection frequency bandwidth of the PAE. Furthermore, the ultrasonic signal, photoacoustic sensing signal, and the pulsed light signal are transmitted through electrical cable, different optical fibers, or media, thus further increasing the size in the endoscopy.

SUMMARY

To address the shortcomings of existing technology, the present disclosure provides an integrated optical waveguide device, an endoscopic probe, and an all-optical PAE sensing system. The integrated optical waveguide device is used to separate tunable light signals from pulsed light signal, enabling each to perform their distinct functions. It utilizes a reflector to output the tunable light signal that carries the sensed information. The device is characterized by its compact structure and the significant refractive index difference of its waveguide. The endoscopic probe, manufactured using this integrated optical waveguide technology, boasts a compact structure, high spatial efficiency, high repetition rate, high sensitivity, high longitudinal resolution, and a small size. Its high level of integration makes it suitable for use in confined and narrow spaces, such as interior cavities, thereby broadening the application scope of the PAE.

The objective of the present disclosure is achieved by the following technical solutions:

The present disclosure provides an integrated optical waveguide device, where a refractive index of a core is greater than that of a cladding;

and, when the refractive index of the substrate is less than that of the core, the integrated optical waveguide device sequentially includes the substrate, the cladding, and the core from bottom to top;

when the refractive index of the substrate is not less than that of the core, the integrated optical waveguide device sequentially includes the substrate, a buffer, the cladding, and the core from bottom to top, with a refractive index of the buffer less than that of the core;

along the light transmission direction, the core sequentially includes a splitter and two connected regions: a first wavelength transmission region and a sensing reflection region;

the splitter is configured to separate light of different wavelengths;

the first wavelength transmission region is configured to transmit pulsed light; and the sensing reflection region is configured to realize transmission, reflection or resonance on a light signal of a preset wavelength, and to monitor changes in the resonant or reflective wavelength, thereby monitoring changes in an environmental parameter.

Furthermore, the first wavelength transmission region is a pulsed light transmission waveguide; and the sensing reflection region is realized in any one of the following manners:

(1) the sensing reflection region includes a straight waveguide, a sensing structure including N microrings with different resonant wavelengths that are cascaded, and a reflection device for changing the light transmission direction, where N is an integer greater than 1, and the microrings have different diameters;

(2) the sensing reflection region includes a sensing structure comprising N asymmetric Mach-Zehnder interferometers with different resonant wavelengths that are cascaded, and a reflection device for changing the light transmission direction, where N is integer greater than1; and (3) the sensing reflection region includes a sensing reflection structure comprising N Bragg gratings with different reflective wavelengths that are cascaded, where N is an integer greater than 1.

Furthermore, the first wavelength transmission region includes a pulsed light transmission waveguide and a grating coupler; and the sensing reflection region is realized in any one of the following manners:

(1) the sensing reflection region comprises a straight waveguide, a sensing structure including N microrings with different resonant wavelengths that are cascaded, and a reflection device for changing the light transmission direction, where Nis an integer greater than 1, and the microrings have different diameters;

(2) the sensing reflection region includes a sensing structure comprising N asymmetric Mach-Zehnder interferometers with different resonant wavelengths and are cascaded, and a reflection device for changing the light transmission direction, where Nis an integer greater than 1; and (3) the sensing reflection region includes a sensing reflection structure comprising N Bragg gratings with different reflective wavelengths that are cascaded, where N is an integer greater than 1.

Further, the sensing structure or the sensing reflection structure may be spiral in overall to achieve a more compact structure.

Further, the reflection device for changing the light transmission direction can be a Sagnac ring; or, the reflection device for changing the light transmission direction consists of a metal film plated at the exit end of the sensing reflection region of the integrated optical waveguide device, so as to ensure that the input end and output end of the integrated optical waveguide device share a single port, thereby reducing the device's structure size.

With either the Sagnac ring or the metal film as the reflection device, the pulsed light signal and the tunable light signal can be simultaneously separated through a single optical fiber and the integrated optical device. The tunable light signal carrying the photoacoustic signal can be reversely transmitted and received, resulting in structurally more compact endoscopic probe with a smaller size.

Furthermore, the cladding material is selected from flexible options such as polydimethylsiloxane (PDMS) film, benzocyclobutene (BCB) film, SU-8 film, and Epoclad film. These elastic films can increase the change of photoacoustic waves or acoustic waves for the effective refractive index of the waveguide device, achieving higher detection sensitivity. They also protect the waveguide, reduce damage and contamination, and lower the transmission loss. The core material is chosen from lithium niobate, silicon (Si), $Si_3N_4$, and chalcogenide. These materials offer a large refractive index difference and low transmission loss, enabling the integrated optical waveguide device to have a more compact structure. They also allow for ultrasonic detection over a large angle range and reduce loss for higher-sensitivity detection.

The present disclosure provides an endoscopic probe that includes the integrated optical waveguide device, further comprising a plastic sleeve, a metal spring, a metal sleeve, and a single-channel double-clad fiber array, as well as a lateral transmission fiber;

the lateral transmission fiber is selected from options such as a coreless fiber or a graded-index (GRIN) multimode fiber, either individually or in combination;

the metal spring, metal sleeve, and single-channel double-clad fiber array are housed within the plastic sleeve, while the integrated optical waveguide device and the lateral transmission fiber are located within the metal sleeve; and the metal spring has one end fixedly connected to the inner end of the plastic sleeve, and the other end fixedly connected to the metal sleeve; the single-channel double-clad fiber array penetrates through the metal spring, extends into the metal sleeve, and is fixedly connected to one end of the integrated optical waveguide device; the other end of the integrated optical waveguide device is fixedly connected to one end of the lateral transmission fiber; the other end of the lateral transmission fiber is processed into an inclined plane to serve as a fully reflecting surface. A metal film for enhancing reflection efficiency is provided on the fully reflecting surface by magnetron sputtering or evaporation.

The present disclosure also provides an endoscopic probe that include the integrated optical waveguide device, where the endoscopic probe further includes a plastic sleeve, a metal spring, a metal sleeve, and a single-channel double-clad fiber array;

the metal spring, metal sleeve, and the single-channel double-clad fiber array are housed within the plastic sleeve, with the integrated optical waveguide device located within the metal sleeve; and the metal spring has one end fixedly connected to the inner end of the plastic sleeve and the other end fixedly connected to the metal sleeve. The single-channel double-clad fiber array penetrates through the metal spring, extends into the metal sleeve, and is fixedly connected to one end of the integrated optical waveguide device.

Additionally, both the connecting end of the single-channel double-clad fiber array and the connecting end of the integrated optical waveguide device are ground and polished to an angle of 8°.

The present disclosure provides an all-optical PAE sensing system based on integrated optical waveguide technology, including a first laser, a fiber-optic polarizer, a polarization controller, a fiber-optic circulator, a second laser, a combiner, a connector, a photoelectric detector, an amplifier, a data acquisition card, a data processing terminal, and an endoscopic probe, where the first laser, the fiber-optic polarizer, and the polarization controller are sequentially connected;

the fiber-optic circulator includes a first port, a second port, and a third port that are connected in a clockwise direction, and is configured to separate a light signal carrying a photoacoustic signal from a narrow-band tunable light signal input to the fiber-optic circulator;

the polarization controller is connected to the first port of the fiber-optic circulator; the combiner is connected to the second port of the fiber-optic circulator; and the third port of the fiber-optic circulator is connected to the photoelectric detector;

an input port of the combiner is further connected to the second laser; and an output port of the combiner, the connector, and the endoscopic probe are connected sequentially;

the photoelectric detector, amplifier, data acquisition card, and data processing terminal are connected sequentially; the photoelectric detector is configured to convert the light signal carrying the photoacoustic signal into an electrical signal; the data acquisition card performs analog-digital conversion on the voltage signal output by the photoelectric detector and upload the converted signal to the data processing terminal; and the data processing terminal processes the information acquired by the data acquisition card, thereby obtaining information of the sample;

an apparatus for rotating and translating the endoscopic probe is built into the connector;

the first laser is a tunable laser or an optical frequency comb, configured to output the light signal for detecting the photoacoustic signal and to convert detection on the photoacoustic signal into measurement on the light signal through the sensing reflection region, thereby improving performance; and the second laser is a pulsed laser.

The present disclosure offers the following beneficial effects:

1. The integrated optical waveguide device provided by the present disclosure features a shared port for both the input end and output end, achieving a smaller size. In addition, the integrated optical waveguide device is capable of performing liquid sensing, biomolecular sensing, and gas sensing. Besides, it can be configured to delay and filter light signals, making it applicable in both optical communication and microwave photonics.

2. According to the endoscopic probe using the integrated optical waveguide device provided by the present disclosure, the photoacoustic light signal and the pulsed light signal shares the same double-clad fiber, thereby reducing a size of the endoscopic probe. The core of the fiber is configured to transmit the sensed light signal, and the inner cladding of the fiber is configured to transmit the pulsed light signal. While device structures and a number of device structures are the same, the scale is smaller, thereby further reducing the size of the endoscopic probe. The endoscopic probe can be used in narrow and small spaces such as interior cavities, thus expanding an application range of the all-optical PAE. Meanwhile, the endoscopic probe using the integrated optical waveguide device can be produced in batches, with a high repetition rate, a high sensitivity, a high longitudinal resolution, a small size, a high level of integration, and a low cost.

3. Compared to the existing technique that use two optical fibers to transmit the sensed light signal and the pulsed light signal separately, the all-optical PAE sensing system provided by the present disclosure utilizes the endoscopic probe with integrated optical waveguide technology. The system employs an all-optical detection method and incorporates the advantages of the double-clad fiber-optic endoscope. The sensed light signal and the pulsed light signal can be transmitted simultaneously through a single optical fiber and effectively separated at the distal end of the endoscopic probe. The bandwidth of light is $10^5$ or more times the bandwidth of the ultrasonic signal. Compared to conventional piezoelectric detectors, the detection method based on the integrated optical waveguide device achieves higher-sensitivity ultrasonic detection over a wider frequency band, providing a greater detection bandwidth. The high-frequency component in the photoacoustic signal is crucial for achieving high axial resolution of PAE. With the greater detection bandwidth, both the axial resolution and the saturation limit of PAE are improved. The sensitivity of the integrated optical device for detecting pressure changes is directly proportional to the quality (Q) factor and wavelength. With a greater Q factor and longer wavelength, detection sensitivity is improved. For example, microring resonance amplifies the effective path length by 1000 times or more, enabling high-sensitivity ultrasonic detection. Therefore, compared to conventional PAE using the piezoelectric transducer, the present disclosure offers higher detection sensitivity, low-noise equivalent pressure, high longitudinal resolution, and high detection frequency bandwidth.

DETAILED DESCRIPTION OF THE EMBODIMENTS

To facilitate understanding of the technical aspects of the present disclosure for those skilled in the art, the contents of the present disclosure will be further explained below with reference to the drawings.
Explanations on technical terms:
PDMS: Polydimethylsiloxane; and
BCB: Benzocyclobutene.

Figure 1:
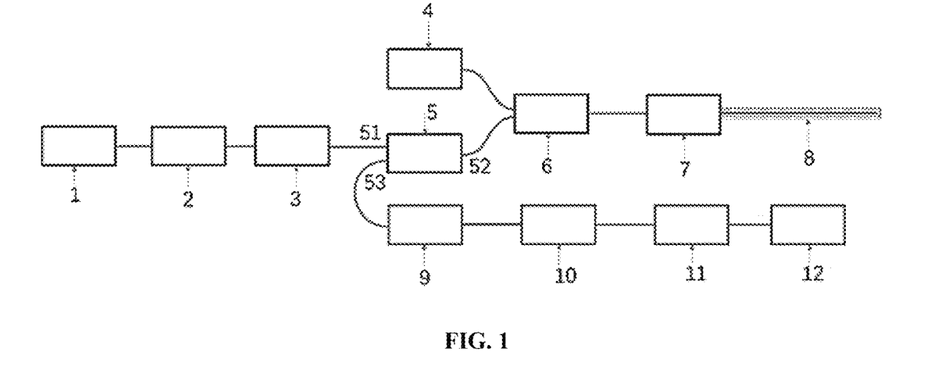
FIG. 1 is a schematic view of an all-optical PAE sensing system based on an integrated optical waveguide technique, according to an embodiment.

Embodiment 1 all-Optical PAE Sensing System Based on Integrated Optical Waveguide Technique As shown in FIG. 1, the all-optical PAE sensing system in the embodiment includes a first laser 1, a fiber-optic polarizer 2, a polarization controller 3, a second laser 4, a fiber-optic circulator 5, a combiner 6, a connector 7, an endoscopic probe 8, a photoelectric detector 9, an amplifier 10, a data acquisition card 11, and a data processing terminal 12.

The first laser 1, the fiber-optic polarizer 2, and the polarization controller 3 are connected sequentially. The fiber-optic circulator 5 includes a first port 51, a second port 52, and a third port 53, which are connected in a clockwise direction. And it is configured to separate a light signal carrying a photoacoustic signal from a narrow-band tunable light signal input into the fiber-optic circulator 5. The polarization controller 3 is connected to the first port 51 of the fiber-optic circulator 5. The combiner 6 is connected to the second port 52 of the fiber-optic circulator 5. The third port 53 of the fiber-optic circulator 5 is connected to the photoelectric detector 9. An input port of the combiner 6 is further connected to the second laser 4. An output port of the combiner 6, the connector 7, and the endoscopic probe 8 are connected sequentially. The photoelectric detector 9, the amplifier 10, the data acquisition card 11, and the data processing terminal 12 are connected sequentially. The second laser 4 is a pulsed laser with a central wavelength of 532 nm. A near-infrared light signal with a wavelength within 600-900 nm is focused on a sample. The sample absorbs laser energy to instantaneously induce thermoelastic expansion, followed by emitting ultrasonic waves in a wide frequency range. By detecting these ultrasonic waves, a diagram showing optical absorption contrasts of the sample is constructed. These ultrasonic waves are transmitted to the integrated optical device, such that the integrated optical waveguide device changes in geometrical shape and refractive index, thereby changing an effective refractive index of the core. When the resonant wavelength is circulated in the microring, the change of a path length of the microring is accumulated. The amplified change of the path length can be quantified by measuring a displacement of the resonant wavelength. The displacement of the resonant wavelength can be converted by a tunable narrow band laser into a light intensity for modulation. The first laser 1 is a tunable laser or an optical frequency comb, with a central wavelength of 1550 nm, and is configured to output the light signal for detecting the photoacoustic signal, and convert, through a sensing reflection region, detection on the photoacoustic signal into measurement on the light signal. With the photoacoustic or ultrasonic detection sensitivity directly proportional to a Q factor of the integrated optical waveguide device, and directly proportional to a wavelength output by the tunable laser for resonance, the integrated optical waveguide device achieves the higher sensitivity. The speed of light oscillation is $10^5$ or more times the speed of the ultrasonic wave. The detection method based on the integrated optical device allow for high-sensitivity ultrasonic or photoacoustic detection over a wide frequency band, thereby improving the axial resolution and the functional saturation limit of the system.

The tunable light signal output from the first laser 1 passes through the fiber-optic polarizer 2, the polarization controller 3, and the port 51 of the fiber-optic circulator 5 sequentially, and is output from the second port 52 of the fiber-optic circulator 5. The tunable light signal is combined through the combiner 6 with the pulsed light signal output from the second laser 4, thereby entering the fiber-optic endoscopic probe 8 through the connector 7. When the pulsed light output from the fiber-optic endoscopic probe 8 irradiates the sample, it induces instantaneous thermal expansion and generates pressure waves. These waves are received by the integrated optical waveguide device within the fiber-optic endoscopic probe 8. The light signal carrying the pressure waves is transmitted sequentially through the endoscopic probe 8 and the connector 7, passes through the connector 7, the combiner 6, and the second port 52 of the fiber-optic circulator 5, the light signal is output from the third port 53, and detected by the photoelectric detector 9. Through the amplifier 10 and the data acquisition card 11, an offset of a resonant wavelength or a reflective wavelength is detected and processed by the data processing terminal 12, thus obtaining tomographic information or functional information of the sample. Meanwhile, an apparatus for rotating and translating the endoscopic probe is built in the connector 7. The connector 7 is driven by a direct current (DC) motor to rotate, thereby rotating the endoscopic probe 8. Through the connector, the endoscopic probe 8 is translated from the proximal end to the distal end, and the operation that the endoscopic probe 8 is pulled back is realized.

Embodiment 2 First Endoscopic Probe

Figure 2:
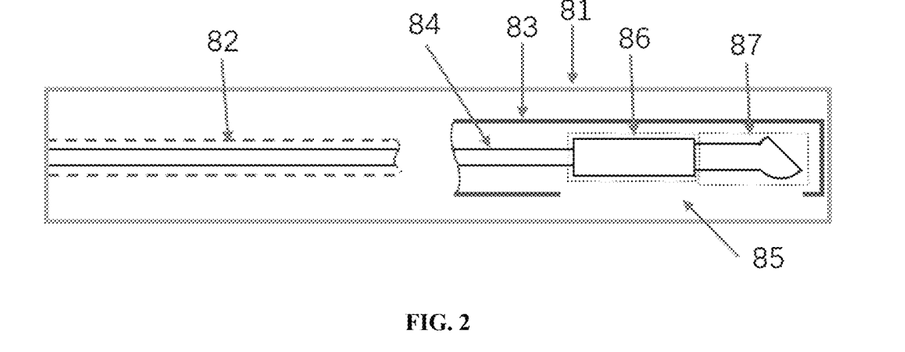
FIG. 2 is a schematic structural view of an endoscopic probe provided with a lateral transmission fiber 87, with the integrated optical waveguide device enclosed by a red dotted line.

As shown in FIG. 2, in the embodiment, the endoscopic probe 8 includes plastic sleeve 81, metal spring 82, metal sleeve 83, single-channel double-clad fiber array 84, integrated optical waveguide device 86, and lateral transmission fiber 87. The plastic sleeve 81 is transparent. Glass sleeve 840 is sleeved on the single-channel double-clad fiber array 84. Cutting hole 85 is formed at a side of the metal sleeve 83 toward a sample. The lateral transmission fiber 87 is selected from any one or a combination of a coreless fiber and a GRIN multimode fiber.

The integrated optical waveguide device 86 is located at a distal end of the endoscopic probe 8. The integrated optical waveguide device 86, the lateral transmission fiber 87, the glass sleeve 840, and a part of the single-channel double-clad fiber array 84 are encapsulated in the metal sleeve 83 having the cutting hole 85. A remaining part of the single-channel double-clad fiber array 84 is encapsulated in the metal spring 82, so as to protect an optical fiber, and make the optical fiber flexible. A tail end of the metal sleeve 83 having the cutting hole 85 is connected to the metal spring 82 by soldering. A tail end of the metal spring 82 is connected to the single-channel double-clad fiber array 84 by soldering. The whole endoscopic probe is encapsulated by the transparent plastic sleeve 81. This prevents the probe from directly contacting the sample in the test, protects the endoscopic probe, and facilitates disinfection. A distal end of the lateral transmission fiber 87 is specially processed into an inclined plane to serve as a fully reflecting surface. A metal film for reinforcing reflection efficiency is provided on the fully reflecting surface by magnetron sputtering or evaporation, so as to irradiate the sample laterally. Each part in the endoscopic probe 8 is connected by an ultraviolet curing adhesive.

In combination with Embodiment 1, the endoscopic probe has the following working principle: The pulsed light from the second laser 4 is transmitted by an inner cladding of the single-channel double-clad fiber array 84 of the endoscopic probe 8. The tunable light signal from the first laser 1 is transmitted by a core of the single-channel double-clad fiber array 84 of the endoscopic probe 8. The double-clad fiber is coupled with the integrated optical waveguide device 86 through the glass sleeve 840. The pulsed light signal and the tunable light signal passing through the single-channel double-clad fiber array 84 are coupled to enter the integrated optical waveguide device 86, and separated through the integrated optical waveguide device. The pulsed light signal is output from the integrated optical waveguide device 86 and transmitted to the lateral transmission fiber 87. An end surface of the distal end of the lateral transmission fiber 87 is fired by a fiber fusion splicer into a ball. One side of the fired ball is ground and polished into an angle of 43°-47°. The fully reflecting surface is a plane. In order to reduce aberration, a light exit surface is ground and polished into a plane. In order to further improve total reflection efficiency, a metal film may be plated on the ground and polished plane for total reflection. The metal film may be a chromium film and a gold film, that are respectively plated in a cavity of a magnetron sputtering instrument and a cavity of a thermal evaporator. The metal film can reinforce the total reflection of the light signal on the interface. The pulsed light output from the lateral transmission fiber 87 irradiates the sample laterally through the transparent plastic sleeve 81. After absorbing light of a specific wavelength, the sample generates heat, such that local temperature build-up and thermal expansion of the sample are caused to emit ultrasonic waves. These ultrasonic waves are acted on the integrated optical waveguide device 86, such that the integrated optical waveguide device 86 deforms to change its refractive index. These ultrasonic waves are loaded on the tunable light signal, returned to the core of the single-channel double-clad fiber array 84 of the endoscopic probe 8 for transmission, and returned to the system through the connector 7 for processing.

Embodiment 3 Second Endoscopic Probe

Figure 3:
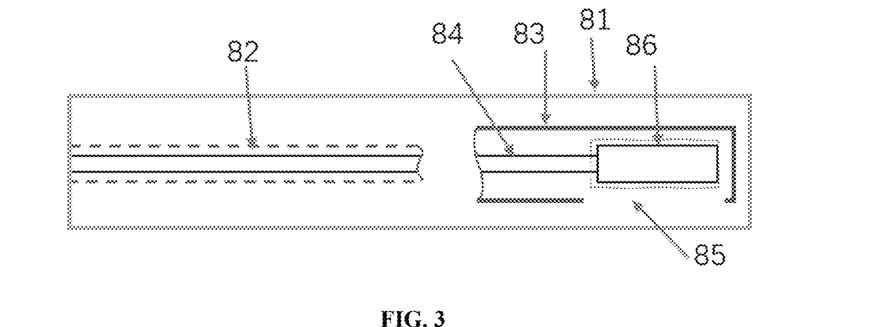
FIG. 3 is a schematic structural view of an endoscopic probe not provided with a lateral transmission fiber 87, with the integrated optical waveguide device enclosed by a red dotted line.

As shown in FIG. 3, unlike Embodiment 2, the fiber-optic part of the endoscopic probe 8 in the embodiment includes only the single-channel double-clad fiber array 84, but not the lateral transmission fiber 87, provided that the integrated optical waveguide device 86 of the endoscopic probe 8 includes a grating coupler (for example, as in Embodiment 5, Embodiment 6, and Embodiment 7), and other compositions and structures are the same as those in Embodiment 2. In terms of the working principle, unlike Embodiment 2, the pulsed light signals separated by the integrated optical waveguide device 86 irradiates the sample laterally through a grating diffraction effect of the grating coupler 860-5 in the integrated optical waveguide device 86. This interaction triggers an immediate thermal expansion within the sample, leading to the generation of pressure waves. The generated pressure waves, in turn, impact the integrated optical waveguide device 86, causing modulation of the tunable light signal. The modulated signals return to the core of the single-channel double-clad fiber array 84 of the endoscopic probe 8 for transmission, and return to the system through the connector 7 for processing.

Embodiment 4 First Integrated Optical Waveguide Device

Figure 4:
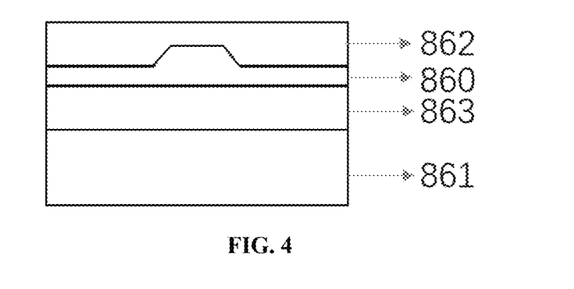
FIG. 4 is a schematic cross-sectional view of a four-layer integrated optical waveguide device.
Figure 5:
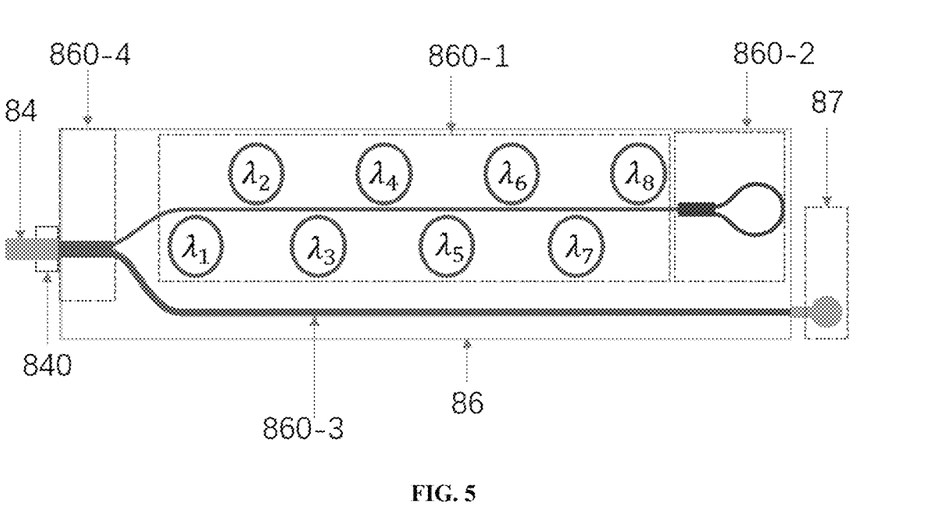
FIG. 5 is a schematic structural view of an integrated optical device with cascaded microrings 860-1 as a sensing region, and a Sagnac ring 860-2 as a reflection device.
Figure 6:
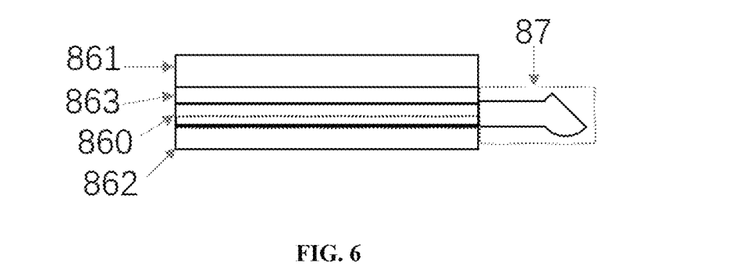
FIG. 6 is a schematic structural view illustrating the relative positions of a longitudinal section of an integrated optical device and a lateral transmission fiber during testing.

As shown in FIG. 4, in the embodiment, the integrated optical waveguide device 86 sequentially includes substrate 861, buffer layer 863, core layer 860, and cladding layer 862 from bottom to top. The core 860 is made of lithium niobate. The substrate 861 is made of Si. The cladding 862 is made of PDMS. The buffer 863 is made of silicon dioxide. As shown in FIG. 5, along a light transmission direction, the core 860 sequentially includes splitter 860-4, as well as first wavelength transmission region 860-3 and a sensing reflection region connected to the splitter 860-4. In the embodiment, the first wavelength transmission region 860-3 is a pulsed light transmission waveguide. The sensing reflection region includes a straight waveguide, sensing structure 860-1 with eight microrings cascaded, and a reflection region composed of Sagnac ring 860-2. Resonant wavelengths $\lambda_1$, $\lambda_2$, $\lambda_3$, $\lambda_4$, $\lambda_5$, $\lambda_6$, $\lambda_7$, and as of the eight microrings are respectively 1550 nm, 1553.2 nm, 1556.4 nm, 1559.6 nm, 1562.8 nm, 1546.8 nm, 1543.6 nm, and 1540.4 nm. Pulsed light transmitted by the pulsed light transmission waveguide has a central wavelength of 532 nm. At an output end of the integrated optical waveguide device 86, the pulsed light transmission waveguide is coupled to the lateral transmission fiber 87 of the endoscopic probe through an ultraviolet curing adhesive, with a connected position as shown in FIG. 6. When the pulsed light output from the lateral transmission fiber 87 irradiates the sample, thermal expansion of the sample is induced instantaneously to generate photoacoustic waves. The photoacoustic waves are acted on the integrated optical waveguide device 86 in the endoscopic probe 8 through an intermediate medium. The pressure waves are acted on the eight microrings, such that the effective refractive index of the cascaded microring resonator changes, and the resonant wavelength is deviated. Through the Sagnac ring 860-2 and the eight microrings, the Q factor of the cascaded microrings is improved, with the steeper filtering edge and the narrower pulse width. The returned light signal leaves away from the integrated optical waveguide device 86 through the splitter 860-4. With the integrated optical waveguide device 86, the measurement on the photoacoustic waves or the acoustic waves is converted into the measurement on the offsets of the resonant wavelengths. By measuring offsets of the resonant wavelengths of the eight microrings, the pressure waves are measured, thereby obtaining the structural or functional information of the sample.

Embodiment 5 Second Integrated Optical Waveguide Device

Figure 7:
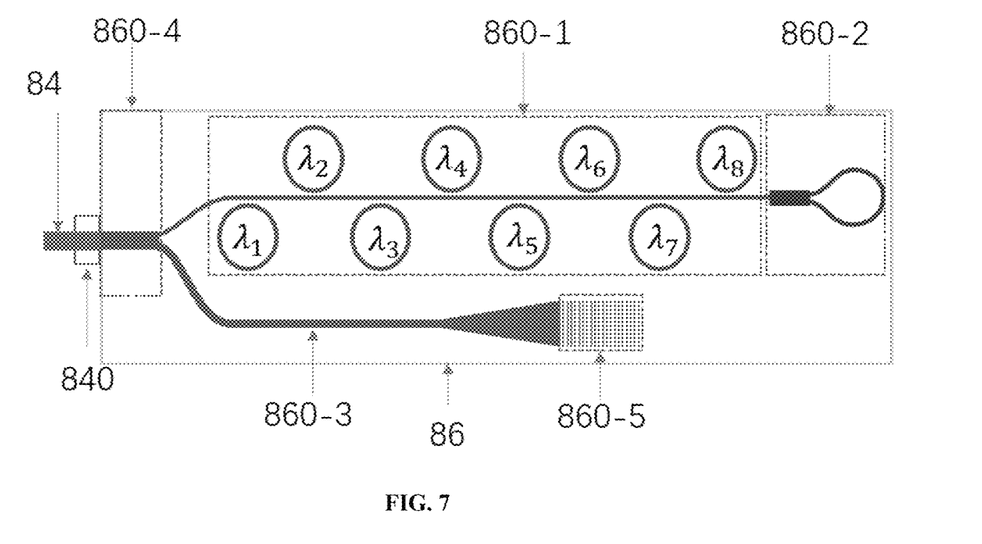
FIG. 7 is a schematic structural view of an integrated optical device with a grating coupler 860-5 as a pulsed light signal emitting end, cascaded microrings 860-1 as a sensing region, and a Sagnac ring as a reflection device.

As shown in FIG. 7, in the embodiment, the integrated optical waveguide device 86 differs from Embodiment 4, in that the first wavelength transmission region 860-3 further includes a grating coupler 860-5 connected to the tail end of the pulsed light transmission waveguide, beside the pulsed light transmission waveguide. Through grating diffraction, the pulsed light leaves the integrated optical waveguide device 86 to irradiate the sample. Other contents are the same as those in Embodiment 4.

Embodiment 6 Third Integrated Optical Waveguide Device

Figure 8:
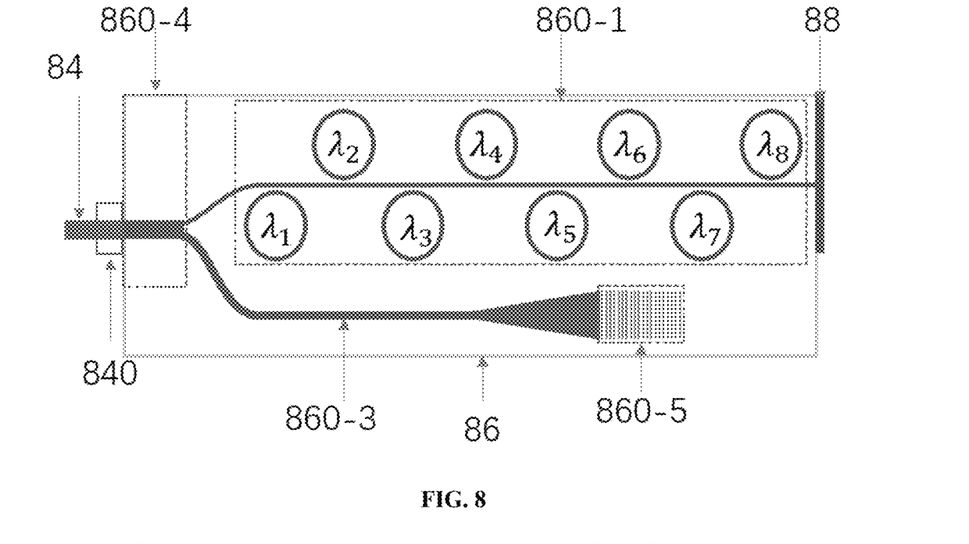
FIG. 8 is a schematic structural view of an integrated optical device with a grating coupler 860-5 as a pulsed light signal emitting end, a metal film reflector 88, and cascaded microrings 860-1 as a sensing region.

As shown in FIG. 8, in the embodiment, the integrated optical waveguide device 86 different from Embodiment 5 in that the Sagnac ring 860-2 in the sensing reflection region is replaced by metal film reflector 88. The metal film reflector 88 changes the light transmission direction. The light signal carrying information of the photoacoustic waves is transmitted to the system, thereby demodulating structural or functional information of the sample.

Embodiment 7 Fourth Integrated Optical Waveguide Device

Figure 9:
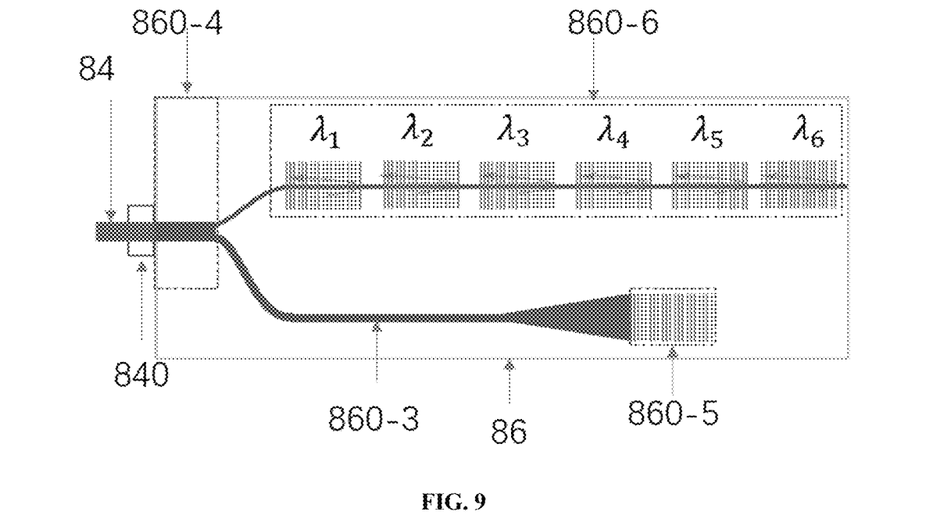
FIG. 9 is a schematic structural view of an integrated optical device with a grating coupler 860-5 as a pulsed light signal emitting end, and cascaded Bragg gratings as a sensing reflection region, with a red arrow indicating light reflection.

As shown in FIG. 9, in the embodiment, the first wavelength transmission region 860-3 of the integrated optical waveguide device 86 is structurally identical to those in Embodiment 5 and Embodiment 6. However, the sensing reflection region is equipped with cascaded Bragg gratings 860-6. Reflective wavelengths $\lambda_1$, $\lambda_2$, $\lambda_3$, $\lambda_4$, $\lambda_5$, and $\lambda_6$ of six cascaded Bragg gratings are respectively 1550 nm, 1556.4 nm, 1562.8 nm, 1569.2 nm, 1543.6 nm, and 1537.2 nm. When the pulsed light irradiates the sample, thermal expansion of the sample is instantaneously induced, generating photoacoustic waves. These photoacoustic waves act on the sensing reflection region of the endoscopic probe 8, causing the effective refractive index of the integrated optical waveguide device 86 to change, and consequently altering the reflective wavelengths of the six cascaded Bragg gratings 860-6. By this time, the measurement of the photoacoustic waves or acoustic waves is transformed into a measurement of the offsets of reflective wavelengths. By measuring the offsets of the reflective wavelengths of the six Bragg gratings, the pressure waves acted on the integrated optical waveguide device are measured, thereby obtaining the structural or functional information of the sample.

Embodiment 8 Fifth Integrated Optical Waveguide Device

Figure 10:
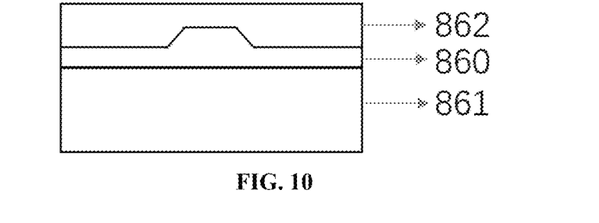
FIG. 10 is a schematic cross-sectional view of a three-layer integrated optical waveguide device.

As shown in FIG. 10, in the embodiment, the integrated optical waveguide device 86 sequentially includes a substrate 861, a core 860, and a cladding 862 from bottom to top. The core 860 is made of lithium niobate. The substrate 861 is made of silicon dioxide. The cladding 862 is made of PDMS. The structure on the core is identical to that in Embodiment 4.

Those of ordinary skill in the art will understand that the embodiments described herein are intended to help readers understand the principles of the present disclosure, and it should be understood that the protection scope of the present disclosure is not limited to such special statements and embodiments. Various changes and modifications may be made to the present disclosure by those skilled in the art. Any modification, equivalent substitution and improvement made within the spirit and principle of the present disclosure should fall within the protection scope of the claims of the present disclosure.

The invention claimed is:

1. An integrated optical waveguide device, wherein a refractive index of a core is greater than a refractive index of a cladding;

and, when a refractive index of a substrate is less than the refractive index of the core, the integrated optical waveguide device sequentially comprises the substrate, the cladding, and the core from bottom to top;

when the refractive index of the substrate is not less than the refractive index of the core, the integrated optical waveguide device sequentially comprises the substrate, a buffer, the cladding, and the core from bottom to top; and a refractive index of the buffer is less than the refractive index of the core;

along a light transmission direction, the core sequentially comprises a splitter, as well as a first wavelength transmission region and a sensing reflection region that are connected to the splitter;

the splitter is configured to separate light of different wavelengths;

the first wavelength transmission region is configured to transmit pulsed light; and the sensing reflection region is configured to realize transmission, reflection or resonance on a light signal of a preset wavelength, and to monitor a change in a resonant wavelength or a reflective wavelength, thereby monitoring a change in an environmental parameter.

2. The integrated optical waveguide device according to claim 1, wherein the first wavelength transmission region is a pulsed light transmission waveguide; and the sensing reflection region is realized in any one of the following manners:

(1) the sensing reflection region comprises a straight waveguide, a sensing structure comprising N microrings that have different resonant wavelengths and are cascaded, and a reflection device for changing the light transmission direction, wherein N is an integer greater than 1; and the microrings have different diameters; and (2) the sensing reflection region comprises a sensing reflection structure comprising N Bragg gratings that have different reflective wavelengths and are cascaded, wherein N is an integer greater than 1.

3. The integrated optical waveguide device according to claim 1, wherein the first wavelength transmission region comprises a pulsed light transmission waveguide and a grating coupler; and the sensing reflection region is realized in any one of the following manners:

(1) the sensing reflection region comprises a straight waveguide, a sensing structure comprising N microrings that have different resonant wavelengths and are cascaded, and a reflection device for changing the light transmission direction, wherein N is an integer greater than 1; and the microrings have different diameters; and (2) the sensing reflection region comprises a sensing reflection structure comprising N Bragg gratings that have different reflective wavelengths and are cascaded, wherein Nis an integer greater than 1.

4. The integrated optical waveguide device according to claim 2, wherein the reflection device for changing the light transmission direction is a Sagnac ring; or, the reflection device for changing the light transmission direction is a metal film plated at an exit end of the sensing reflection region of the integrated optical waveguide device, so as to ensure that an input end and an output end of the integrated optical waveguide device share a single port, thereby reducing a structure size of the device.

5. The integrated optical waveguide device according to claim 1, wherein a material of the cladding is selected from any one of a flexible polydimethylsiloxane (PDMS) film, a benzocyclobutene (BCB) film, and a SU-8 film; and a material of the core is selected from any one of lithium niobate, silicon (Si), $Si_3N_4$, and chalcogenide.

6. An endoscopic probe comprising the integrated optical waveguide device according to claim 2, wherein the endoscopic probe further comprises a plastic sleeve, a metal spring, a metal sleeve, a single-channel double-clad fiber array, and a lateral transmission fiber;

the lateral transmission fiber is selected from any one or a combination of a coreless fiber and a graded-index (GRIN) multimode fiber;

the metal spring, the metal sleeve, and the single-channel double-clad fiber array are housed within the plastic sleeve; and the integrated optical waveguide device and the lateral transmission fiber are located within the metal sleeve; and the metal spring has one end fixedly connected to an inner end of the plastic sleeve, and the other end fixedly connected to the metal sleeve; the single-channel double-clad fiber array penetrates through the metal spring, extends into the metal sleeve, and is fixedly connected to one end of the integrated optical waveguide device; the other end of the integrated optical waveguide device is fixedly connected to one end of the lateral transmission fiber; the other end of the lateral transmission fiber is processed into an inclined plane to serve as a fully reflecting surface; and a metal film for enhancing reflection efficiency is provided on the fully reflecting surface by magnetron sputtering or evaporation.

7. An endoscopic probe comprising the integrated optical waveguide device according to claim 3, wherein the endoscopic probe further comprises a plastic sleeve, a metal spring, a metal sleeve, and a single-channel double-clad fiber array;

the metal spring, the metal sleeve, and the single-channel double-clad fiber array are housing within the plastic sleeve; and the integrated optical waveguide device is located within the metal sleeve; and the metal spring comprises one end fixedly connected to an inner end of the plastic sleeve, and the other end fixedly connected to the metal sleeve; and the single-channel double-clad fiber array penetrates through the metal spring, extends into the metal sleeve, and is fixedly connected to one end of the integrated optical waveguide device.

8. The endoscopic probe according to claim 6, wherein both a connecting end of the single-channel double-clad fiber array and a connecting end of the integrated optical waveguide device are ground and polished into an angle of 8°.

9. An all-optical photoacoustic endoscopy (PAE) sensing system based on integrated optical waveguide technology, comprising a first laser, a fiber-optic polarizer, a polarization controller, a fiber-optic circulator, a second laser, a combiner, a connector, a photoelectric detector, an amplifier, a data acquisition card, a data processing terminal, and the endoscopic probe according to claim 6, wherein the first laser, the fiber-optic polarizer, and the polarization controller are sequentially connected;

the fiber-optic circulator comprises a first port, a second port, and a third port that are connected in a clockwise direction, and is configured to separate a light signal carrying a photoacoustic signal from a narrow-band tunable light signal input to the fiber-optic circulator;

the polarization controller is connected to the first port of the fiber-optic circulator; the combiner is connected to the second port of the fiber-optic circulator; and the third port of the fiber-optic circulator is connected to the photoelectric detector;

an input port of the combiner is further connected to the second laser; and an output port of the combiner, the connector, and the endoscopic probe are connected sequentially;

the photoelectric detector, the amplifier, the data acquisition card, and the data processing terminal are connected sequentially; the photoelectric detector is configured to convert the light signal carrying the photoacoustic signal into an electrical signal; the data acquisition card is configured to perform analog-digital conversion on the electrical signal output by the photoelectric detector and upload a converted signal to the data processing terminal; and the data processing terminal is configured to process information acquired by the data acquisition card, thereby obtaining information of a sample;

an apparatus for rotating and translating the endoscopic probe is built in the connector;

the first laser is a tunable laser or an optical frequency comb, and configured to output the light signal for detecting the photoacoustic signal, and convert detection on the photoacoustic signal into measurement on the light signal through the sensing reflection region, thereby improving performance; and the second laser is a pulsed laser.

10. The integrated optical waveguide device according to claim 3, wherein the reflection device for changing the light transmission direction is a Sagnac ring; or, the reflection device for changing the light transmission direction is a metal film plated at an exit end of the sensing reflection region of the integrated optical waveguide device, so as to ensure that an input end and an output end of the integrated optical waveguide device share one port to reduce a device structure.

11. The endoscopic probe according to claim 7, wherein both a connecting end of the single-channel double-clad fiber array and a connecting end of the integrated optical waveguide device are ground and polished into an angle of 8°.

12. An all-optical photoacoustic endoscopy (PAE) sensing system based on integrated optical waveguide technology, comprising a first laser, a fiber-optic polarizer, a polarization controller, a fiber-optic circulator, a second laser, a combiner, a connector, a photoelectric detector, an amplifier, a data acquisition card, a data processing terminal, and the endoscopic probe according to claim 7, wherein the first laser, the fiber-optic polarizer, and the polarization controller are sequentially connected;

the fiber-optic circulator comprises a first port, a second port, and a third port that are connected along a clockwise direction, and is configured to separate a light signal carrying a photoacoustic signal from a narrow-band tunable light signal input to the fiber-optic circulator;

the polarization controller is connected to the first port of the fiber-optic circulator; the combiner is connected to the second port of the fiber-optic circulator; and the third port of the fiber-optic circulator is connected to the photoelectric detector;

an input port of the combiner is further connected to the second laser; and an output port of the combiner, the connector, and the endoscopic probe are connected sequentially;

the photoelectric detector, the amplifier, the data acquisition card, and the data processing terminal are connected sequentially; the photoelectric detector is configured to convert the light signal carrying the photoacoustic signal into an electrical signal; the data acquisition card is configured to perform analog-digital conversion on a voltage signal output by the photoelectric detector and upload a converted signal to the data processing terminal; and the data processing terminal is configured to process information acquired by the data acquisition card, thereby obtaining information of a sample;

an apparatus for rotating and translating the endoscopic probe is built in the connector;

the first laser is a tunable laser or an optical frequency comb, and configured to output the light signal for detecting the photoacoustic signal, and convert, through the sensing reflection region, detection on the photoacoustic signal into measurement on the light signal, thereby improving performance; and the second laser is a pulsed laser.

* * * * *